(12) United States Patent
Nelson et al.

(10) Patent No.: US 7,396,687 B2
(45) Date of Patent: *Jul. 8, 2008

(54) MASS SPECTROMETRIC IMMUNOASSAY ANALYSIS OF SPECIFIC PROTEINS AND VARIANTS PRESENT IN VARIOUS BIOLOGICAL FLUIDS

(75) Inventors: Randall W. Nelson, Phoenix, AZ (US); Peter Williams, Phoenix, AZ (US); Jennifer Reeve Krone, Granbury, TX (US)

(73) Assignee: Intrinsic Bioprobes, Inc., Tempe, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/958,867

(22) Filed: Oct. 4, 2004

(65) Prior Publication Data

US 2005/0153311 A1    Jul. 14, 2005

Related U.S. Application Data

(63) Continuation of application No. 09/855,143, filed on May 14, 2001, now abandoned, which is a continuation-in-part of application No. 09/024,988, filed on Feb. 17, 1998, which is a continuation of application No. 08/449,903, filed on May 23, 1995, now abandoned.

(51) Int. Cl.
    *G01N 24/00* (2006.01)
(52) U.S. Cl. .................. 436/173; 435/7.1; 435/7.92; 436/518; 436/524
(58) Field of Classification Search .......... 435/6, 435/7.1, 7.92, 961, 973; 436/501, 518, 524, 436/541, 173, 174, 177

See application file for complete search history.

(56) References Cited

U.S. PATENT DOCUMENTS

| | | | | |
|---|---|---|---|---|
| 4,770,774 | A | * | 9/1988 | Ida et al. ............... 210/259 |
| 5,437,979 | A | * | 8/1995 | Rampal et al. ............ 435/6 |
| 5,538,897 | A | * | 7/1996 | Yates et al. ............. 436/89 |
| 5,605,798 | A | * | 2/1997 | Koster ................. 435/6 |
| 5,894,063 | A | * | 4/1999 | Hutchens et al. ......... 436/155 |
| 6,974,704 | B2 | * | 12/2005 | Nelson et al. ........... 436/173 |

FOREIGN PATENT DOCUMENTS

GB    2030294 A    4/1980

OTHER PUBLICATIONS

Gaskell, Quantification of steroid conjugates using fast atom bombardment mass spectrometery, Steroids, 1990, vol. 55, October, pp. 458-462.*
Papac et al., Direct Analysis of Affinity-Bound Analytes by MALDI/TOF MS, Anal. Chem. 1994, 66, 2609-2613.*
UniXL, Two Dimensional techniques—Gas Liquid Chromatography & Mass Spectrometry, http://www.unixl.com/dir/molecular-sciences/chemsitry/analytica/chemistry/two.dimens..., pp. 1-2, 2005.*
Duncan et al., Quantitative Analysis of Low Molecular Weight Compounds of Biological Interest by Matrix-assisted Laser Desorption Ionization, Rapid Communications in Mass Spectrometry, vol. 7, 1090-1094, 1993.*
Nuwaysir et al., Electrospray Ionization Mass Spectrometry of Phosphopeptides Isolated by On-line Immobilized Metal-Ion Affinity Chromatography, J Am Soc Mass Spectrom 1993, 4, 662-669.*
Bieber et al., Mass Spectrometric Immunoassay, Anal. Chem. 1995, 67, 1153-1158.

* cited by examiner

*Primary Examiner*—Long V. Le
*Assistant Examiner*—Gary W Counts
(74) *Attorney, Agent, or Firm*—Snell & Wilmer L.L.P.

(57) ABSTRACT

Presented herein is the construction of pipettor tips (termed MSIA-Tips) containing porous solid supports that are constructed, covalently derivatized with affinity ligand, and used to extract specific proteins and their variants from various biological fluids by repeatedly flowing the fluids through the MSIA-Tips. A second protein species (a mass-shifted variant of the targeted protein doped into the samples at a constant concentration) is co-extracted with the endogenous protein and variants and is used as a quantitative internal reference standard (IRS). Nonspecifcally bound compounds are rinsed from the MSIA-Tip using a series of buffer and water rinses, after which the wild type protein, protein variants and the IRS are eluted from the MSIA-Tips directly onto a target in preparation for analysis such as MALDI-TOF. Mass spectrometry of the eluted sample then follows with the retained proteins identified via accurate molecular mass determination. Protein and variant levels are determined via a quantitative method in which the protein/variant signals are normalized to the signal of the IRS and the values compared to a working curve constructed from samples containing known concentrations of the protein or variants.

4 Claims, 5 Drawing Sheets

MASS SPECTROMETRIC IMMUNOASSAY ANALYSIS OF SPECIFIC PROTEINS AND VARIANTS PRESENT IN VARIOUS BIOLOGICAL FLUIDS

CROSS REFERENCE TO RELATED APPLICATION

This application is a continuation of application Ser. No. 09/855,143 filed May 14, 2001, now abandoned, which is a continuation-in-part of pending application Ser. No. 09/024,988 filed on Feb. 17, 1998, which was a continuation of original application Ser. No. 08/449,903, which was filed on May 23, 1995, now abandoned, the disclosure of which is incorporated herein by reference.

FIELD OF THE INVENTION

The present invention is related to the field of proteomics and diagnostics. More specifically, the present invention covers devices and methods for the rapid identification and characterization of biomolecules recovered directly from biological fluid. The devices and methods according to the present invention include the ability to identify proteins and their variants using mass spectrometry. Additionally, the present invention provides for mass spectrometric immunoassay kits for the qualitative and quantitative analysis of specific proteins and variants present in various biological fluids.

BACKGROUND OF THE INVENTION

With the recent first draft completion of the human genome, much attention is now shifting to the field of proteomics, where gene products (proteins), their various variants, interacting partners and the dynamics of their regulation and processing are the emphasis of study. Such studies are essential in understanding, for example, the mechanisms behind genetic/environmentally induced disorders or the influences of drug mediated therapies, as well as potentially becoming the underlying foundation for further clinical and diagnostic analyses. Critical to these studies is the ability to qualitatively determine specific variants of whole proteins (i.e., splice variants, point mutations and posttranslationally modified versions) and the ability to view their quantitative modulation.

Traditionally, distinctly different assays are used in the qualitative analysis of proteins/variants and in monitoring their quantitative modulation. Qualitative analyses generally rely on structurally related techniques such as NMR or X-Ray crystallography, or, oftentimes, are accomplished on the gene level through gene sequencing or various methodologies of single nucleotide polymorphism analyses. Quantitative analyses rely, more so, on functional related properties of the proteinaceous analyte, and include various immunoassays (enzyme-linked immunosorbent assays and radioimmunoassays) or biosensor type instrumentation. As such, there is a lack in any one assay to qualitatively differentiate between different variants of a specific protein while still maintaining quantitative capabilities.

As an example, $\beta$-2-microglobulin ($\beta_2$m) is a low molecular mass protein identified as the light chain of the Class I major histocompatibility complex synthesized in all nucleated cells. Upon activation of the immune system, both B- and T-lymphocytes actively release $\beta_2$m into circulation where it is later eliminated via glomerular filtration and tubular reabsorption. Serum levels of $\beta_2$m have been measured and nominally correlated to ailments such as AIDS, rheumatoid arthritis, leukemia, myeloma and malignant lymphoma. On the other hand, $\beta_2$m levels in urine are indicators of glomerular filtration rate and tubular reabsorption. Conventionally, $\beta_2$m levels are monitored using a variety of immuno-based assays, including enzyme-linked immunosorbent assays, radioimmunoassays and particle-enhanced turbidimetry assays. The quantitative dynamic range (spanning $\beta_2$m concentrations of ~0.2-20 mg/L) and the accuracy (1-10%) of the assays are sufficient to cover the normal and elevated levels of $\beta_2$m in a variety of biological fluids. One drawback of these conventional assays, however, is the inability to differentiate between the wild type and variants of $\beta_2$m. Such distinction is important when considering that genetic and posttranslational variants of $\beta_2$m are indicative of ailments distinct from those indicated by the wild type protein. Several separate assays are thus required to discern between these different protein variants, and to date, no such combination of assays has been used in the study of $\beta_2$m.

Thus, there exists a need for a single assay capable of assessing proteins present in a variety of biological fluids, both qualitatively and quantitatively. New and novel technologies are needed to fulfill these needs. Importantly, these technologies must: 1) be able to selectively retrieve and concentrate specific proteins/biomarkers from biological fluid for subsequent high-performance analyses, 2) be able to quantify targeted proteins, 3) be able to recognize variants of targeted proteins (e.g., splice variants, point mutations and posttranslational modifications) and to elucidate their nature, and 4) be capable of analyzing for, and identifying, ligands interacting with targeted proteins.

Two protein mass spectrometry techniques, matrix-assisted laser desorption/ionization time-of-flight mass spectrometry (MALDI-TOF MS) and electrospray ionization mass spectrometry, offer the particular advantage of differentiating between different mass-shifted forms of the same protein. In this manner, a single pan-antibody can be used to retrieve all protein variants from a biological fluid, upon which each variant is detected during mass spectrometry at a unique and characteristic molecular mass. Mass resolution of related species also allows mass-shifted variants of a target protein to be intentionally incorporated into the analysis for use as internal reference standards for quantitative analysis. This step forms the basis of a mass spectrometric immunoassay (MSIA), an assay that can be used for the unambiguous detection and rigorous quantification of polypeptides/proteins retrieved from complex biological systems.

For the foregoing reasons, there is a need for MSIA devices, methods and kits for the rapid and efficient analysis of specific proteins and variants present in various biological fluids.

SUMMARY OF THE INVENTION

It is an object of the present invention to construct devices that prepare micro-samples directly from biological fluid to be used in detecting and quantifying proteins present in several biological fluids.

It is another object of the present invention to construct pipettor tips (termed MSIA-Tips) containing porous solid supports that are constructed, covalently derivatized with affinity ligand, and used to extract specific proteins and their variants from various biological fluids by repeatedly flowing the fluids through the MSIA-Tips. A second protein species (a mass-shifted variant of the targeted protein doped into the samples at a constant concentration) is co-extracted with the endogenous protein and variants and is used as a quantitative internal reference standard (IRS). Nonspecifically bound compounds are rinsed from the MSIA-Tip using a series of buffer and water rinses, after which the wild type protein, protein variants and the IRS are eluted from the MSIA-Tips directly onto a target in preparation for analysis such as MALDI-TOF. Mass spectrometry of the eluted sample then follows with the retained proteins identified via accurate molecular mass determination. Protein and variant levels are determined via a quantitative method in which the protein/variant signals are normalized to the signal of the IRS and the values compared to a working curve constructed from samples containing known concentrations of the protein or variants.

It is yet another object of the invention to provide an assay that using MSIA-Tips and associated methods that has an adequate quantitative dynamic range, accuracy, and linearity to cover the concentrations of proteins expected in the biological fluids.

A further object of this present invention enables useful product kits for specific proteins and variants detection, qualification, and quantification of samples directly from biological fluids, as demonstrated herein.

The present invention includes the ability to selectively retrieve and concentrate specific biomolecules from biological fluid for subsequent high-performance analyses (e.g. MALDI-TOF MS), the ability to identify targeted biomolecules, the ability to quantify targeted biomolecules, the ability to recognize variants of targeted biomolecules (e.g., splice variants, point mutations and posttranslational modifications) and to elucidate their nature, and the capability to analyze for, and identify, ligands interacting with targeted biomolecules.

The novel features that are considered characteristic of the invention are set forth with particularity in the appended claims. The invention itself, however, both as to its structure and its operation together with the additional objects and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 D.S.C. §112, paragraph 6 to define the invention. To the contrary, if the provisions of 35 D.S.C. §112, paragraph 6, are sought to be invoked to define the invention (s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 D.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

FIG. 2. $\beta_2$-microglobulin MSIA screening of biological fluids. Samples were prepared by dilution of the biological fluid with HBS ($H_2O$ for standalone MALDI-TOF) and repetitive flow incubation through the MSIA-Tip. MSIA-Tips were washed using HBS and water before elution of retained compounds directly onto a mass spectrometer target using ACCA (saturated in 1:2, $ACN:H_2O$; 0.2% TFA). (A) Human tears. (B) Human plasma. (C) Human saliva—the saliva required an additional rinse with 0.05% SDS (in water) to reduce non-specific binding. (D) Human urine. In all cases, $\beta_2$m was efficiently retrieved from the biological fluids using the flow-incubate/rinse procedure. The masses determined for the $\beta_2$m (using external calibration) were within ~0.1% of the calculated value ($MW_{calc}$=11,729.7; $MW_{tears}$=11,735; $MW_{plasma}$=11734; $MW_{saliva}$=11,742; $MW_{urine}$=11,735).

FIG. 3. Quantitative $\beta_2$m-MSIA—working curve. (A) Representative spectra of data used to generate the working curve. Human $\beta_2$m concentrations of 0.01-1.0 mg/L were investigated. Equine $\beta_2$m (MW=11,396.6) was used as an internal standard. (B) Working curve generated using the data represented in (A). The two-decade range was spanned with good linearity ($R^2$=0.983). Error bars reflect the standard deviation often repetitive 65-laser shots spectra taken from each sample. (Inset) Historesis effect noticed in the serial dilution of the $\beta_2$m standards. Data from the second decade dilution is normalized and overlayed onto the data from the first decade dilution. The curves show roughly the same effect throughout the dilution, which is due to mis-calibrated pipettors and is ultimately responsible for the overall relative error of the working curve (~9%).

DESCRIPTION OF THE PREFERRED EMBODIMENTS

The present invention provides for methods, devices and kits for the MSIA analysis of specific proteins and variants present in various biological fluids.

Another embodiment of the present invention provides for the construction of MSIA-Tips that exhibit a low degree of non-specific binding properties in various biological fluids.

Yet another embodiment of the present invention provides for the detection of specific proteins and variants present in various biological fluids.

Another embodiment of the present invention provides for methods used in the quantification of proteins and variants present in various biological fluids.

Yet another embodiment of the present invention provides for the use of MSIA in screening of individuals or large populations for specific proteins and variants present in various biological fluids.

In yet another embodiment, the present invention provides for MSIA kits capable of fulfilling the previous embodiments.

Specific embodiments in accordance with the present invention will now be described in detail using the following lexicon. These examples are intended to be illustrative, and the invention is not limited to the materials, methods or apparatus set forth in these embodiments.

As used herein, "MSIA-Tips" refers to a pipettor tip containing an affinity reagent.

As used herein, "affinity reagent" refers to a molded, porous, high surface area base support containing a low dead-volume (e.g. <2 µL of unused volume) to which affinity ligands are immobilized. The composition of the base support may be, but is not limited to, glasses, silica glasses, silica, silicon, plastics, polymers, metals, or any combination of these materials and the like. Affinity ligands are immobilized to the base support through the process of chemical activation.

As used herein "chemically activate" refers to the process of exposing the affinity reagent to chemicals in order to subsequently attach tethering linkers and/or affinity ligands. Compounds able to activate affinity reagents may be, but are not limited to organic or inorganic reagents. Often, it is advantageous to activate the affinity reagent base support using multiple steps including the use of a tethering linker. As used herein, "tethering linker" refers to compounds intermediate to the base support and the affinity ligand that exhibit the desirable characteristics of being able to be derivatized with high densities of affinity ligand and showing low binding of non-specified compounds. The tethering linker may be intrinsically active or require activation for attachment. Suitable tethering compounds include, but are not limited to, homo/ hetero functional organics, natural and synthetic polymers, and biopolymers.

As used herein, "affinity ligand" refers to atomic or molecular species having an affinity towards analytes present in biological mixtures. Affinity ligands may be organic, inorganic or biological by nature, and can exhibit broad (targeting numerous analytes) to narrow (target a single analyte) specificity. Examples of affinity ligands include, but are not limited to, receptors, antibodies, antibody fragments, synthetic paratopes, enzymes, proteins, multi-subunit protein receptors, mimics, chelators, nucleic acids, and aptamers.

As used herein, "analyte" refers to molecules of interest present in a biological sample. Analytes may be, but are not limited to, nucleic acids, DNA, RNA, peptides, polypeptides, proteins, antibodies, protein complexes, carbohydrates or small inorganic or organic molecules having biological function. Analytes may naturally contain sequences, motifs or groups recognized by the affinity ligand or may have these recognition moieties introduced into them via chemical or enzymatic processes.

As used herein, "biological fluid" refers to a fluid or extract having a biological origin. Biological fluid may be, but are not limited to, cell extracts, nuclear extracts, cell lysates or biological products used to induce immunity or substances of biological origin such as excretions, blood, sera, plasma, urine, sputum, tears, feces, saliva, membrane extracts, and the like.

As used herein, "internal reference standard" refers to analyte species that are modified (either naturally or intentionally) to result in a molecular weight shift from targeted analytes and their variants. The IRS can be endogenous in the biological fluid or introduced intentionally. The purpose of the IRS is that of normalizing all extraction, rinsing, elution and mass spectrometric steps for the purpose of quantifying targeted analytes and/or variants.

As used herein, "posttranslational modification" refers to any polypeptide alteration that occurs after synthesis of the chain. Posttranslational modifications may be, but are not limited to, glycosylations, phosphorylations, and the like.

As used herein, "mass spectrometer target" refers to an apparatus onto or into which analytes are deposited for subsequent mass spectrometric analysis. Generally, targets will accommodate numerous samples and are of various geometrical configurations depending on the nature of the mass spectrometer for which they are designed. Suitable materials for constructing targets include metals, glasses, plastics, polymers, composites, and the like or combinations thereof.

As used herein, "mass spectrometer" refers to a device able to volatilize/ionize analytes to form vapor-phase ions and determine their absolute or relative molecular masses. Suitable forms of volatilization/ionization are laser/light, thermal, electrical, atomized/sprayed and the like or combinations thereof. Suitable forms of mass spectrometry include, but are not limited to, Matrix Assisted Laser Desorption/Time of Flight Mass Spectrometry (MALDI-TOF MS), electrospray (or nanospray) ionization (ESI) mass spectrometry, or the like or combinations thereof.

EXAMPLE 1

MSIA Analysis of Specific Proteins Present in Biological Fluids

Figure 1:
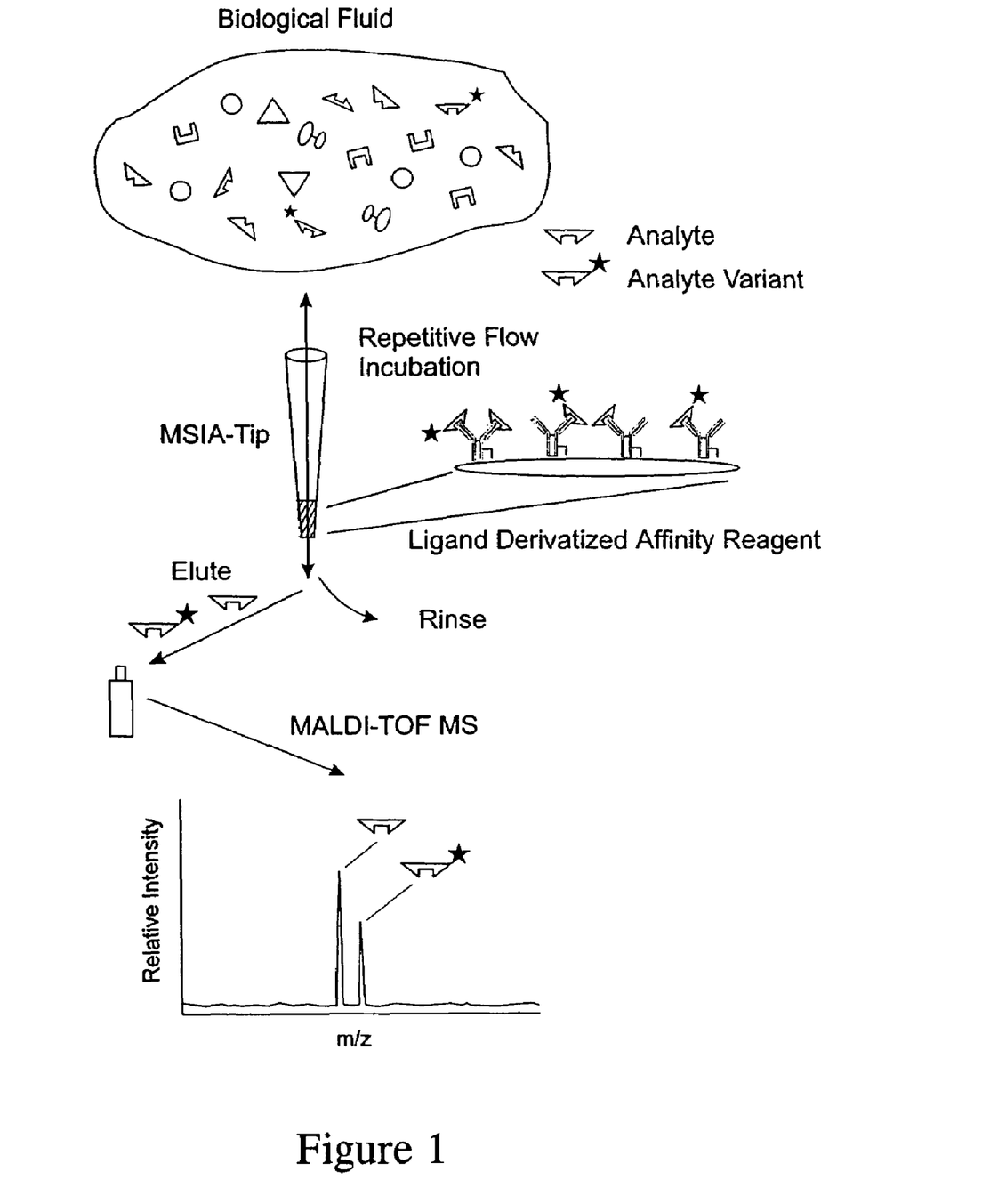
FIG. 1. Illustration of the MSIA procedure. Analytes are selectively retrieved from solution by repetitive flow through a, affinity ligand-derivatized affinity reagent constructed at the entrance of pipettor tip (MSIA-Tip). Once washed of the nonspecifically bound compounds, the retained species are eluted onto a mass spectrometer target using a MALDI matrix. MALDI-TOF MS then follows, with analytes detected at precise m/z values. The analyses are qualitative by nature but can be made quantitative by incorporating mass-shifted variants of the analyte into the procedure for use as internal standards.

The general MSIA approach is shown graphically in FIG. 1. MSIA-Tips, containing porous solid supports covalently derivatized with affinity ligands are used to extract the specific proteins and their variants from biological samples by repeatedly flowing the samples through the MSIA-Tips. A mass-shifted variant of the specific protein, present in the samples at a constant concentration, is co-extracted with the endogenous protein and variants, and is used as a quantitative internal reference standard—normalizing all incubations, extraction, and subsequent rinsing, elution/deposition and mass spectrometric steps in the MSIA process. Nonspecifically bound compounds are rinsed from the MSIA-Tips by using a series of buffer and water rinses, after which retained proteins, variants and the internal reference standard are eluted from the MSIA Tip directly onto a MALDI-TOF target. MALDI-TOF mass spectrometry then follows, identifying the retained proteins via exact molecular mass determination. Moreover, protein and variant levels are determined using a quantitative method in which the protein or variant signals are normalized to the signal of the internal reference standard and the values compared to a working curve constructed from samples containing known concentrations of the protein or variant.

EXAMPLE 2

MSIA-Tip Manufacture

Affinity reagents for the MSIA-Tips were manufactured to the specifications of commercially available pipettor tips (Coast Scientific, CA, PT 0340-BYN) by using annealing molds made of stainless steel (type 446; 100-150 holes of 0.071 inch (entrance) per mold; 2-degree taper, polished and treated with graphite release agent). The molds were loaded with soda lime glass spherical beads (150-200 µm; 75% $SiO_2$, 15% $Na_2O$ and 10% CaO; Sigma, St. Louis, Mo.) and annealing was achieved in an argon-backfilled furnace by ramping the temperature from 772° C. (equilibrated, t=O) to 800° C. (t=3 minutes; equilibrate for one-minute). Upon completion of the ramp-anneal, the molds were immediately removed from the furnace and the affinity reagents taken out. The process yielded affinity reagents with high-flow characteristics and appropriate bore and taper to fit the entrance of the pipette tips (room temperature affinity reagent dimensions: 0.061 in. (entrance), 0.092 in. (length), 2-degree taper).

The affinity reagents were chemically activated and derivatized in batches (30-50 per batch) using the following protocols prior to packing into the pipettor tips. After acid conditioning (with 0.05 M HCl for 1-hour, air-dried), the affinity reagents were treated with 10% amino-propyl triethoxysilane (Aldrich, Milwaukee, Wis.) in anhydrous toluene for 12-hours, at room temperature. The amine-functionalized affinity reagents were then equilibrated in reaction buffer (100 mM sodium phosphate, pH 4.8, 100 mM NaCl) by air evacuation in the presence of the buffer. After equilibration, the buffer was replaced with a mixture of 15 kDa molecular mass carboxylated dextran (CMD, Fluka, Milwaukee, Wis.) and 1-ethyl-3-(3dimethylaminopropyl)carbodiimide (EDC, Sigma, St. Louis, Mo.) (10 mg/mL each in the reaction buffer) and the air was again evacuated from the reaction vessel. The reaction was allowed to proceed for 1 hour (with two subsequent additions of EDC to the reaction mixture at ~20 and 40 minutes into the reaction) before terminating and rinsing. Prior to coupling of the antibody, the CMD-amplified affinity reagents were rinsed vigorously with 100 mM sodium phosphate, pH 8.0, 0.5 M NaCl. The affinity reagents were then chemically activated for 10-minutes with EDC/N-hydroxy succinimide (NHS, Sigma, St. Louis, Mo.) (100 mM each, in $H_2O$) and incubated with the affinity purified rabbit anti-human $\beta_2$m IgG (DAKO, Carpinteria, Calif.) (0.1 mg/mL, in 20 mM sodium acetate, pH 4.7). Uncoupled antibody was removed by extensive rinsing with HBS buffer (10 mM HEPES pH 7.4, 0.15 M NaCl, 0.005% Surfactant P20). The anti-$\beta_2$m MSIA-Tips were found to be stable and active for a period of at least one-month following antibody immobilization (by storing at 4° C. in HBS buffer).

EXAMPLE 3

MSIA of Biological Fluids

All fluids were obtained immediately prior to use; protease inhibitor cocktail (PIC, Protease Inhibitor Cocktail Set III, Calbiochem, La Jolla, Calif.) was added immediately in order to minimize possible proteolytic degradation of $\beta_2$m.

Tears: Human tears were collected by washing the eye with doubly distilled water (dd$H_2O$) and collecting the rinse. A 20 µL of the eye rinse was mixed with 180 µL HBS buffer and used as stock tears solution. This stock was further diluted by a factor of ten with either water (for a standalone MALDI-TOF analysis) or HBS buffer (for MSIA analysis).

Plasma: A 44.7 µL of human whole blood was collected from a lancet-punctured finger using a heparinized microcolumn (Drummond Scientific Co., Broomall, Pa.), mixed with 205 µL HBS buffer and centrifuged for 30 seconds (at 7,000×g) to pellet the red blood cells. A 50 µL aliquot of the supernatant was mixed with 200 µL HBS and the resulting solution was drawn for MSIA; an aliquot was further diluted (10 fold) with $H_2O$ for MALDI-TOF analysis.

Saliva: Human whole saliva was diluted by a factor of 100 in $H_2O$ or HBS buffer in preparation for MALDI-TOF or MSIA, respectively.

Urine: Human urine was prepared for MALDI-TOF by a 100-fold dilution with dd$H_2O$; a two-fold dilution with HBS buffer for used for MSIA.

MSIA Protocol: MSIA was performed on the various biological fluids by repeatedly drawing the biological fluid (~20 times) through an anti-$\beta_2$m-MSIA-Tip, using a hand-held P-200 micropipettor. After the repetitive-flow incubation, the MSIA-Tip was rinsed with 2 mL of HBS buffer (by drawing the HBS through in 200 µL aliquots and then discarding), followed by a 1 mL rinse with dd$H_2O$ (using the same wash and discard approach). At the final discard of the water rinse, it was checked that all residual water was expelled from the MSIA-Tip. The retained compounds were eluted from the MSIA-Tip by drawing a 3 µL aliquot of matrix solution (saturated solution of α-cyano-4hydroxycinnamic acid (ACCA; Aldrich, Milwaukee, Wis.) in 1:2, acetonitrile:$H_2O$, 0.2% TFA) into the MSIA-Tip (enough to cover the affinity reagent), upon which the matrix/eluent mix was deposited directly onto a MALDI-TOF target. MALDI-TOF mass spectrometry was performed using a mass spectrometer that is known to one of ordinary skill in the arts. Briefly, the instrument uses a two-stage 30 kV (2×1 cm; 15 kV/stage) continuous-extraction source to accelerate ions to the entrance of a 1.4 m flight tube containing an ion guide-wire. Ions generated using a pulsed $N_2$ laser (337 nm) were detected using a hybrid single channel plate/discreet dynode multiplier biased at −3.8 kV. Spectra were recorded using an averaging transient recorder while monitoring individual laser shots using a separate oscilloscope and attenuating laser intensity (in real-time) during acquisition. All spectra were acquired in the positive-ion mode.

Figure 2A:
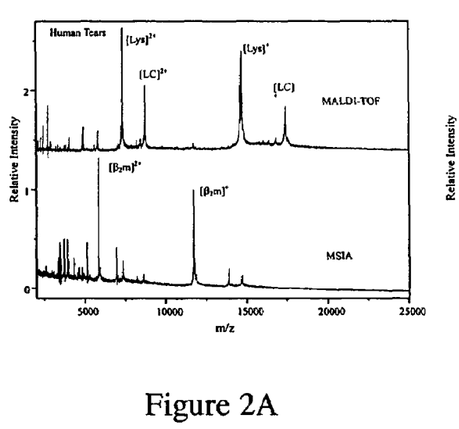
Figure 2B:
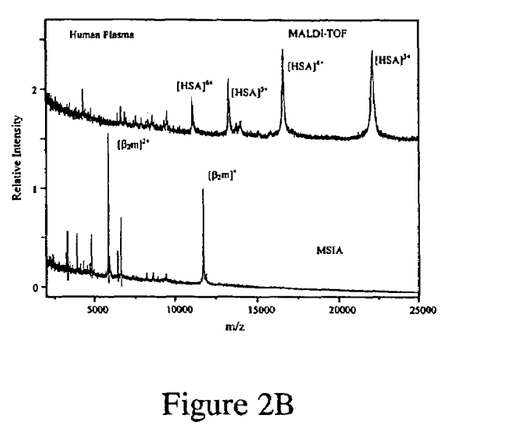
Figure 2C:
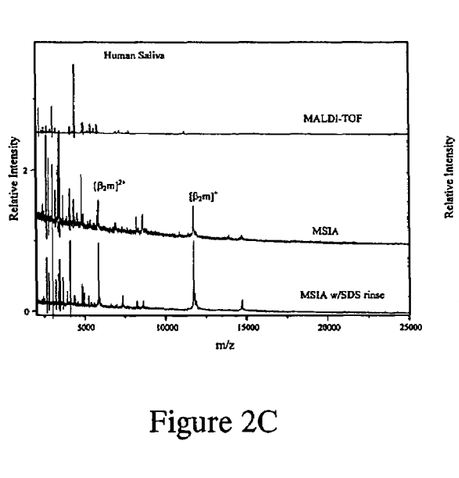
Figure 2D:
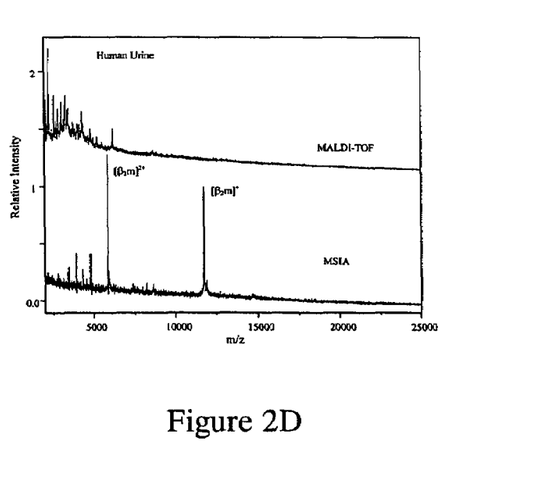

MSIA-Tip Evaluation/Biological Fluids Screening: The MSIA-Tips were evaluated by screening a number of easily obtainable biological fluids to gauge the degree of nonspecific binding encountered from each of the fluids and to briefly investigate alternative rinsing protocols that reduce contributions from non-specific binding. FIG. 2a shows a spectrum of diluted human tear (labeled MALDI-TOF) and a spectrum (labeled MSIA) showing tears compounds retained during MSIA. The MALDI-TOF spectrum is dominated by high-level compounds present in the tears: lysozyme ($MW_{calc}$=14,696; $MW_{obs}$=14,691) and tear lipocalin ($MW_{calc}$=17,444; $MW_{obs}$=17,440). Other polypeptide signals are observed in the 2-5 kDa range, as well as a low-intensity signal at m/z=11,727 Da, presumably due to $\beta_2$m. The MSIA spectrum shows signals due to the selectively retained $\beta_2$m ($MW_{calc}$=11,729; $MW_{obs}$=11,731) and attenuated signals for the lysozyme and other non-specified compounds. FIG. 2b shows MALDI-TOF and MSIA spectra of diluted human plasma. As is commonly observed during direct analysis of serum or plasma, the MALDI-TOF spectrum is dominated by signals originating from albumin. Other, lower m/z signals are also present; however, $\beta_2$m signals are not observed. The MSIA spectrum shows strong signals due to the selectively retained β$_2$m and few other signals from non-specified compounds. FIG. 2c shows spectra of diluted saliva (MALDI-TOF) and saliva compounds retained during MSIA. The MALDI-TOF spectrum shows a number of signals in the 1-18 kDa range, most prominently in the peptide region; signals corresponding to β$_2$m are not observed. The MSIA spectrum, obtained after using the normal rinse protocols, shows signals due to the selectively retained β$_2$m and an abundance of non-specified compounds in the low molecular mass range. A second MSIA analysis in which an additional rinse with 0.05% sodium dodecylsulfate (SDS) was incorporated between the HBS and the H$_2$O rinses was also performed (FIG. 2c). The SDS rinse, although not completely eliminating the low-mass signals, did significantly reduce their contribution to the mass spectrum, without a proportional reduction of the β$_2$m signal. FIG. 2d shows spectra resulting from the analysis of human urine. The MALDI-TOF spectrum shows a number of signals in the peptide region and an absence of signal for β$_2$m. The MSIA spectrum shows predominantly signals from the β$_2$m, with few additional signals from non-specified compounds.

The porous glass affinity reagents in the MSIA-Tips performed exceptionally well during the screens. Intermediate CMD amplification of the glass affinity reagents provided a largely hydrophilic surface with multiple attachment points (carboxyl groups) for coupling to the antibody. As a result, the antibody load of each MSIA-Tip is estimated at 1-100 pmole, which is more than sufficient to capture β$_2$m at subnanomolar concentrations without saturation of the antibody. Also, the hydrophilic surface can be washed free of most non-specifically bound compounds by rinsing with aqueous ionic buffers. With the exception of the saliva sample, MSIA exhibited reasonably clean mass spectra, showing predominantly signals derived from β$_2$m. The SDS wash of the saliva screen, although improving spectral quality, did not completely eliminate all of the non-specified compounds. Upon closer investigation, it is found that those compounds (identified by mass as lysozyme, α-defensins and histatins) have pIs of ~10, suggesting retention via charge interactions (with free-carboxyl groups) that are not broken by the moderate pH (7.8) and salt (150 mM NaCl) content of the HBS buffer. Thus, other rinsing combinations (e.g., high-salt or different detergents) will need to be investigated if the salivary screen is deemed to be of biological significance. It is worth noting, however, that the presence of the non-specified compounds (in any of the samples) did not interfere with the unambiguous determination of β$_2$m, which was identified by virtue of direct detection at its characteristic molecular mass.

EXAMPLE 4

Quantification of Specific Proteins and Variants in Biological Fluids

Quantification: Protein quantification using MALDI-TOF requires use of internal standards to compensate for varying laser intensities and spot-to-spot differences in sample composition that give rise to fluctuations in analyte ion signal. Although proteins with characteristics unlike those of the analyte may be used as internal standards (as has been shown during protein quantification directly from mixtures or during MALDI-TOF quantification of affinity-retrieved species by addition of an internal reference standard to peptides eluted from beaded affinity reagent), internal reference standards that behave similarly to the analyte during laser desorption/ionization are generally preferred. This prerequisite is met during MSIA by choosing internal reference standards that share sequence homology with the target protein: enzymatic/chemically-modified versions of the targeted protein, truncated/extended recombinant forms of the target proteins, the (same) target protein recombinantly expressed in isotopically-enriched media (e.g., $^{15}$N or $^{18}$O), or the same protein from a different biological species. Given that the affinity ligand is able to capture both the target protein and the internal reference standard, MSIA can be designed around a single affinity ligand system. Alternatively, a two-affinity ligand system can be considered where one affinity ligand is used to retrieve the target protein and a separate affinity ligand is used to retrieve the internal reference standard.

Internal reference standard. Equine β$_2$m (Eβ$_2$m) was chosen as an internal reference standard for quantification because of its high degree of similarity to human β$_2$m (Hβ$_2$m) (~75% sequence homology), resolvable mass difference from Hβ$_2$m (MW$_{Eβ2m}$=11,402.9; MW$_{Hβ2m}$=11,729.7) and because it was easily obtainable. Horse urine was collected fresh (at a local stable) and treated immediately with protease inhibitor cocktail. Low solubility compounds were removed from the urine by overnight refrigeration (at 4° C.) followed by centrifugation for 5 minutes at 5,000×g. The urine was then concentrated 20-fold over a 10-kDa MW cut-off filter, with repetitive HBS and water rinses and with several filter exchanges (4 filters/200 mL urine). Treatment of 200 mL fresh urine resulted in 10 mL of β$_2$m-enriched horse urine which served as stock internal reference standard solution for ~100 analyses.

Working curve. Quantification of Hβ$_2$m was performed using the following briefly outlined protocols. Standards were prepared by step-wise dilution (i.e., ×0.8, 0.6, 0.4, 0.2 and 0.1, in HBS) of a 1.0 mg/L stock Hβ$_2$m solution to a concentration of 0.1 mg/L; the 0.1 mg/L solution served as stock for an identical step-wise dilution covering the second decade in concentration (0.01-0.1 mg/mL). A blank solution containing no Hβ$_2$m was also prepared. The samples for MSIA were prepared by mixing 100 μL of each of the standards with 100 μL of stock horse urine and 200 μL of HBS buffer. MSIA was performed on each sample as described above, resulting in the extraction and identification of both Eβ$_2$m and Hβ$_2$m. Ten 65-laser-shots MALDI-TOF spectra were taken from each sample, with each spectrum taken from a different location on the target. Care was taken during data acquisition to maintain the ion signals in the upper 50-80% of the y-axis range and to avoid driving individual laser shots into saturation. A transient recorder set for 10-bit y-axis dynamic range was used for data acquisition, resulting in an overall dynamic range (after 65-laser-shots) that approached the manufacturer's quoted dynamic range limit (12-13 bits, as limited by instrument signal-to-noise; Tektronix TDS 520C users manual, Tektronix Corp., Beaverton, Oreg.). Spectra were normalized relative to the Eβ$_2$m signal through baseline integration, and the integral of Hβ$_2$m was determined. Integrals from the ten spectra taken for each calibration standard were averaged and the standard deviation calculated. A calibration curve was constructed by plotting the average of the normalized integrals for each standard versus the Hβ$_2$m concentration.

Figure 3A:
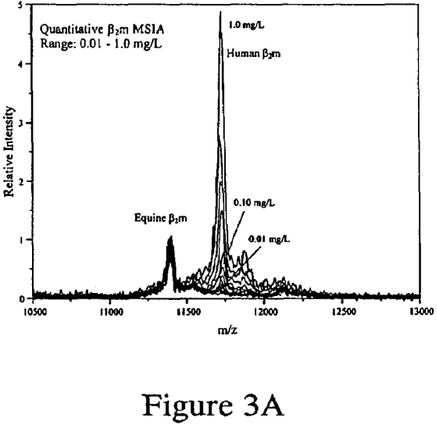

FIG. 3a shows spectra representing MSIA analyses of Hβ$_2$m standards in a concentration range of 0.01-1.0 mg/L. Each spectrum, normalized to the Eβ$_2$m signal, is one of ten 65-laser shots spectra taken for each calibration point. Plotting the average of the 10 normalized Hβ$_2$m integrals for each standard versus the Hβ$_2$m concentration results in the working curve shown in FIG. 3b. Linear regression fitting of the data yields $I_{H\beta 2m}/I_{E\beta 2m}$=4.09[H$\beta_2$m in mg/L]+0.021 ($R^2$=0.983), with a working limit of detection of 0.0025 mg/L (210 pM) and a limit of quantification of 0.01 mg/L (850 pM). The relative error between repetitive mass spectra for each point is low (4-8%), as reflected by the error bars (standard deviation, n=10 spectra) associated with each data point on the working curve. This degree of intra-sample error is significantly lower than the one experienced in past studies and can be attributed to two factors. The first is the use of a high-precision transient recorder (10-bit) yielding approximately a four-fold (2 bit) greater y-axis precision than the one used in our previous studies. The use of this recorder produced mass spectra that, when integrated, contained a relatively large quantity of (digital) data. By maintaining the ion signals in the upper 50-80% of the digital dynamic range, the relative contribution of instrumental noise is reduced, and integrals more accurately reflect the target ion signals. The second factor contributing to high intra-sample reproducibility is the high degree of "sample consistency" experienced using MSIA. Upon elution from the MSIA-Tip onto the mass spectrometer target, the sample/matrix solution is aerated due to the porosity of the affinity capture affinity reagent. This aeration produces a droplet containing a number of small air bubbles that burst as the droplet dries. This sample deposition procedure results in a highly uniform sample over the entire surface of the MS target, allowing high quality spectra to be taken from any spot on the target.

Figure 3B:
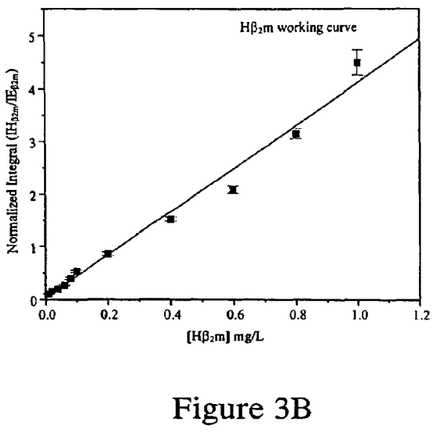

The average relative error (all points) of the working curve is ~9%. This error is mainly due to pipetting errors during the step-wise dilution of the H$\beta_2$m standards. Further inspection of the data points used in generating the working curve show a historesis effect occurring throughout the dilution of the standards. FIG. 3b (inset) shows the six lower points of the working curve normalized to and overlayed upon the upper six points of the curve. The two series show the same effect over the two decades of dilution. Because identical step-wise dilutions were used twice in preparing the standards, the effect is most easily explained by volume errors during dilution of the standards. Such errors are not surprising in that two variable-volume pipettors (Eppendorf P1000 and P200) were used for preparation of the standards. The obvious solution to this problem is to use inter-calibrated fixed-volume pipettors for dilution of standards.

EXAMPLE 5

Screening Individual or Population Samples for Specific Proteins and Variants Present in Biological Fluids Samples: Urine samples were collected from individuals shortly before analysis, treated with protease inhibitor cocktail and cooled to 4° C. The urine samples were centrifuged for 5 minutes (at 3000×g) immediately prior to analysis to remove any precipitated material. In preparation for MSIA, 100 µL of each urine sample was mixed with 100 µL of stock horse urine and 200 µL of HBS. This treatment is identical to that used in preparation of the working curve, with the exception of replacing the standard with the analytical sample (human urine). MSIA was performed as described in the working curve section, with ten spectra taken for each sample and average integrals calculated.

Figure 4:
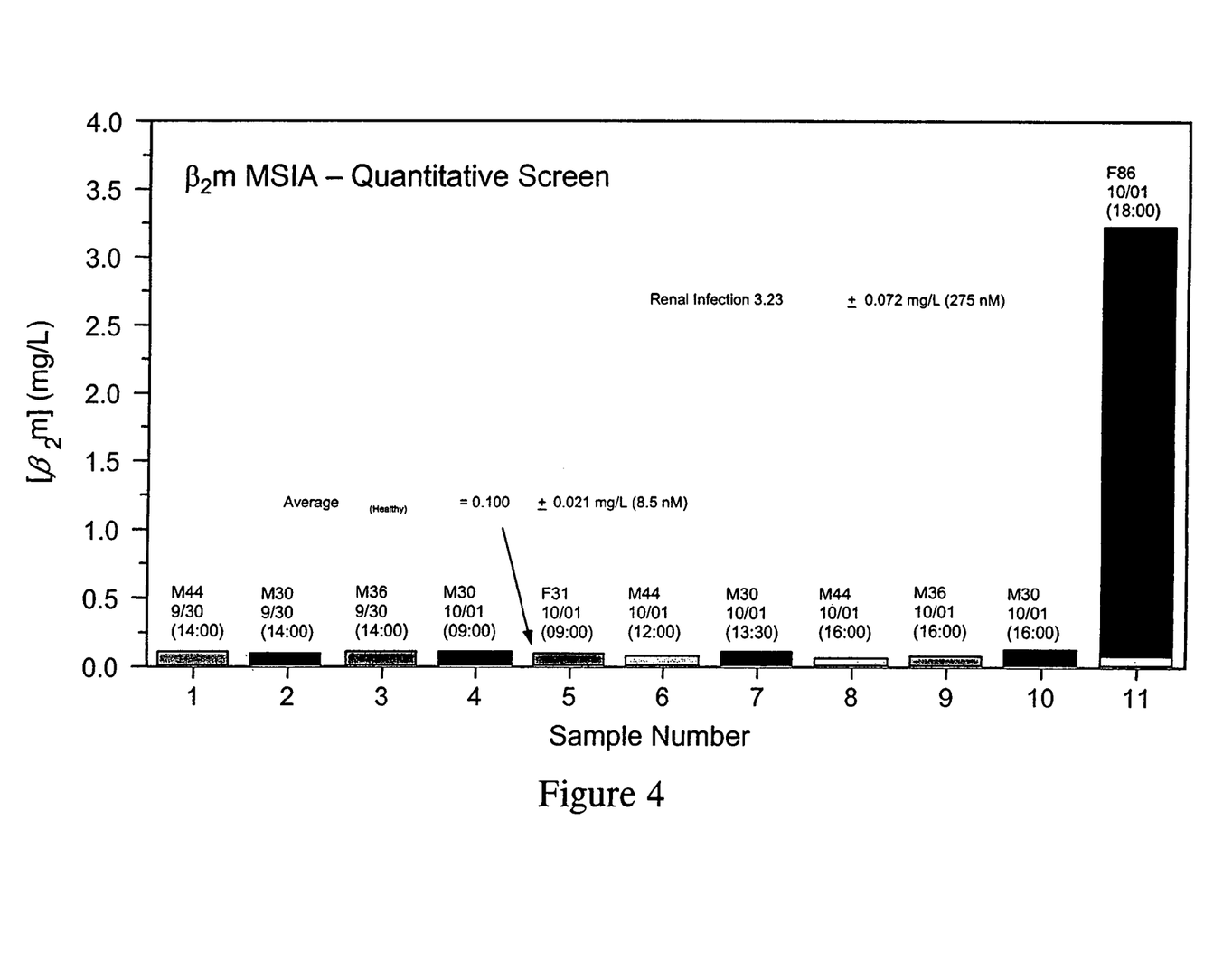
FIG. 4. Quantitative $\beta_2$m-MSIA—screening. Human urine samples from five individuals were screened over a period of two days. The average value determined for healthy individuals (10-samples; 4-individuals (3 male; 1 female) ages 30-44 years) was 0.100±0.021 mg/L. The level determined for an 86-year old female with a recent urinary tract infection indicated a significant increase in $\beta_2$m concentration (3.23±0.072 mg/L).

Quantitative Evaluation of Urines. Ten samples were collected from four individuals: female (31 years, pregnant; 1-sample (F3)), male (30 years; 4-samples over two days (M3)), male (36 years; 2-samples over two days (M3)) and male (44 years; 3-samples over two days (M4)). All of the subjects were in a state of good health when the urines were collected. Results from MSIA of the ten urine samples are shown in FIG. 4. The bars depict the $\beta_2$m concentration determined for each sample, while the inset spectra above each bar show the respective H$\beta_2$m signals normalized to E$\beta_2$m. The data for the ten samples show remarkable consistency, with an average $\beta_2$m concentration of 0.100±0.021 mg/L (high=0.127 mg/L; low=0.058 mg/L). An additional analysis was performed on a urine sample obtained from an 86-year old female (F86) who had recently suffered a renal infection. Because of the significantly higher level of $\beta_2$m found in this sample (see inset spectrum) it was necessary to quantitatively dilute the urine by a factor of ten in order to keep the $\beta_2$m signal inside the dynamic range of the working curve and accurately establish the $\beta_2$m concentration in F86 (at 3.23±0.02 mg/L).

Figure 5:
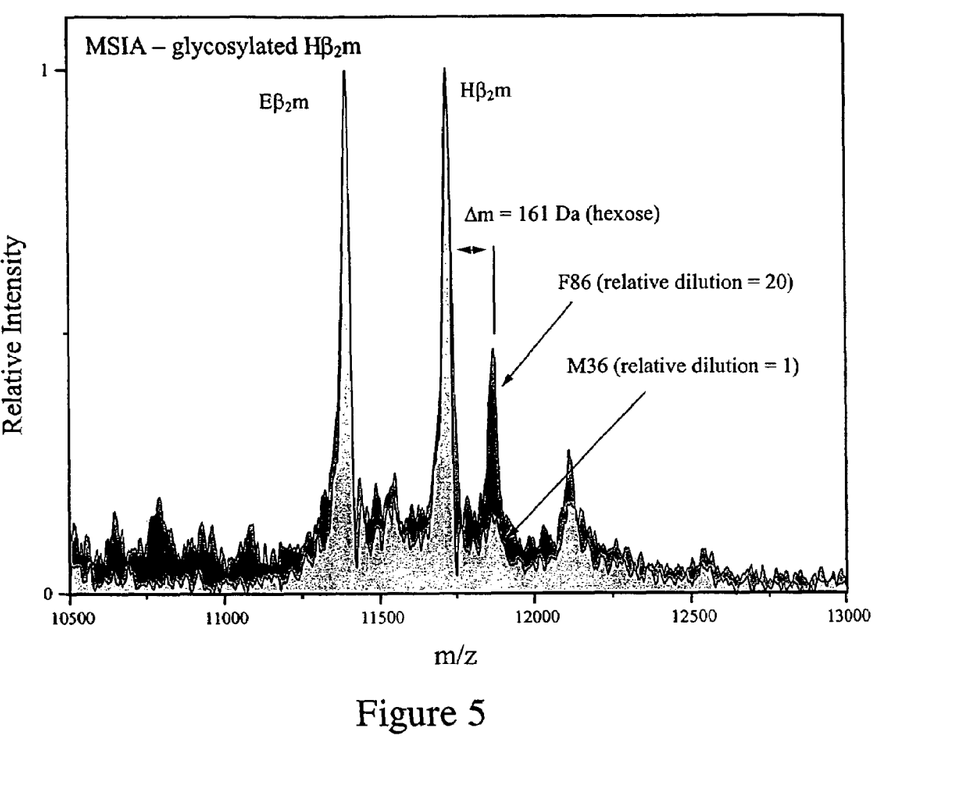
FIG. 5. MSIA showing elevated level of glycosylated $\beta_2$m in a 86-year old female (dark gray). During MSIA, a second signal is observed at $\Delta m$=+161 Da, indicating the presence of glycosylated $\beta_2$m. MSIA is able to adequately resolve the two $\beta_2$m forms, resulting in a more accurate quantification of the nascent $\beta_2$m and possible quantification of the glycoprotein. Such differentiation is important considering that the two $\beta_2$m forms originate from (or are markers for) different ailments. MSIA of a healthy individual, showing little glycosylation, is given for comparison (light gray).

Variant Detection—Posttranslational Modifications. The mass-selective detection of MSIA makes possible the discovery and quantification of variants of $\beta_2$m that may be present in urine. During quantitative screening of the urine samples, a second, higher molecular mass species ($\Delta$m=+161 Da) was co-extracted with the $\beta_2$m. The species is presumably a glycosylated (one hexose) fonn of $\beta_2$m, and is observed most prominently in F86. FIG. 5 shows an overlay of two MSIA spectra taken from the urine of F86 (diluted ×20) and M36 (no dilution; given for comparison). The level of glycosylated $\beta_2$m is much greater in F86 (estimated using the $\beta_2$m-working curve at 0.072 mg/L) than in M36. The specific cause of the elevated level of the glyco-$\beta_2$m is at present uncertain.

EXAMPLE 6

Kits for MSIA of Specific Proteins and Variants Present in Various Biological Fluids The present invention clearly demonstrates the usefulness of MSIA in the analysis of specific proteins and variants present in various biological fluids as well as the need for MSIA kits to expedite and enable the use of MSIA in analysis for specific proteins and variants present in various biological fluids.

Generally, MSIA kits consist of devices, methods and reagents that facilitated the rapid and efficient extraction specific proteins and variants present in various biological fluids. Specifically, MSIA kits may consist of any or all of following items: MSIA-Tips, sample facilitating devices, samples, sample retaining/containment devices, activating reagents, affinity ligands, internal reference standards, buffers, rinse reagents, elution reagents, stabilizing reagents, mass spectrometry reagents and calibrants, mass spectrometry targets, mass spectrometers, analysis software, protein databases, instructional methods, specialized packaging and the like.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for the isolation and subsequent qualitative characterization of a target biomolecule present in biological fluid comprising the steps of:
    a. providing a pipettor tip having an affinity reagent present,
    b. separating and concentrating the target biomolecule directly from the biological fluid by flowing a volume of the biological fluid through the pipettor tip, thereby binding the target biomolecule to the affinity reagent,
    c. releasing the target biomolecule by eluting the target biomolecule from the affinity reagent onto a mass spectrometer target, and
    d. performing a single mass spectrometric analysis using a single mass spectrometer for ionizing the target biomolecule and determining its relative molecular mass in order to qualitatively determine the presence or absence of the target biomolecule in the biological fluid.

2. The method according to claim 1 wherein the qualitative determination further determines a presence of a posttranslational variant of β-2 microglobulin.

3. The method according to claim 1 wherein the affinity reagent further comprises an affinity ligand.

4. The method according to claim 3 wherein the affinity ligand comprises anti-human β-2 microglobulin antibody.

* * * * *